United States Patent [19]
Wei et al.

[11] Patent Number: 5,506,634
[45] Date of Patent: Apr. 9, 1996

[54] FUNDUS ILLUMINATION APPARATUS FORMED FROM THREE, SEPARATED RADIATION PATH SYSTEMS

[75] Inventors: Jay Wei, Fremont; Thomas Hellmuth, Danville, both of Calif.

[73] Assignee: Carl Zeiss, Inc., Thornwood, N.Y.

[21] Appl. No.: 270,750

[22] Filed: Jul. 5, 1994

[51] Int. Cl.⁶ ..................................................... A61B 3/10
[52] U.S. Cl. .......................... 351/221; 351/207; 351/216
[58] Field of Search .................................. 351/200, 205, 351/207, 210, 213, 214, 216, 220, 221

[56] References Cited

U.S. PATENT DOCUMENTS

| | | | |
|---|---|---|---|
| 4,283,124 | 8/1981 | Matsumura | 351/206 |
| 4,572,627 | 2/1986 | Madate et al. | 351/206 |
| 4,666,268 | 5/1987 | Ito | 351/206 |
| 5,067,951 | 11/1991 | Greve | 606/4 |
| 5,116,116 | 5/1992 | Aizu et al. | 351/221 |

FOREIGN PATENT DOCUMENTS 2914675  11/1979  Germany ...................... A61B 3/126

2020846  11/1979  United Kingdom.

OTHER PUBLICATIONS

"Scanning Laser Ophthalmoscope" by R. H. Web and G. W. Hughes, *IEEE Trans. on Biomedical Engineering*, vol. BME–28, No. 7, Jul. 1981, pp. 488–492.

Huang et al., "Optical Coherence Tomography" *Science*, 254, Nov. 22, 1991, pp. 1178–1181.

Primary Examiner—William L. Sikes
Assistant Examiner—Huy Mai
Attorney, Agent, or Firm—Michael B. Einschlag

[57] ABSTRACT

Apparatus for illuminating the fundus of an eye with a scanned sample beam of radiation. An embodiment of the present invention is an optical system which includes three, separated radiation path systems—a tilted illumination path system, a decentered observation path system, and an optical path system—which are combined by a beamsplitter into an ocular lens. In accordance with the present invention, an illuminating path provided by the illumination path system and an optical beam path provided by the optical beam path system are obliquely oriented with respect to the optical axis of the ocular lens.

19 Claims, 5 Drawing Sheets

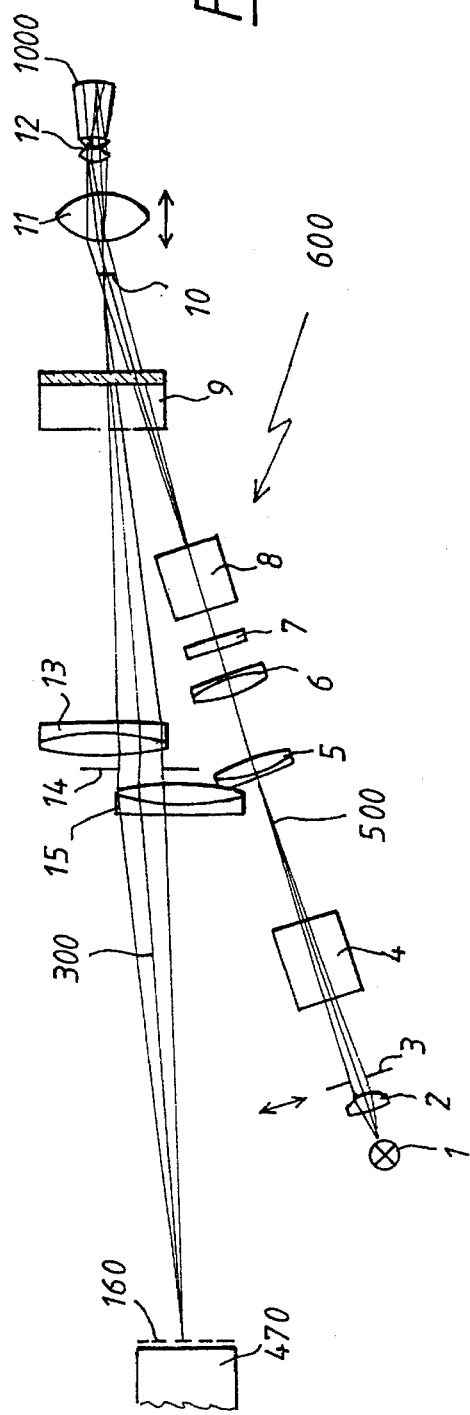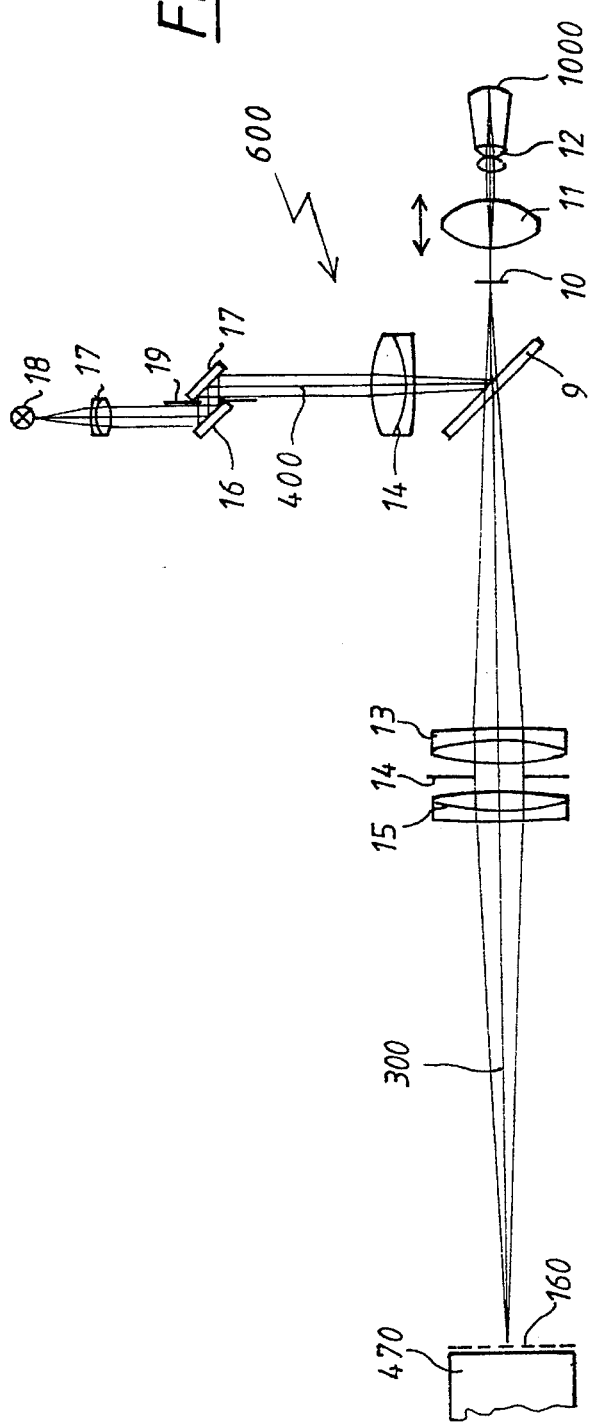

VIGNETTING

FUNDUS ILLUMINATION APPARATUS FORMED FROM THREE, SEPARATED RADIATION PATH SYSTEMS

TECHNICAL FIELD OF THE INVENTION

The present invention relates to an ophthalmologic apparatus for fundus imaging.

BACKGROUND OF THE INVENTION

Present optical systems for fundus imaging, i.e., systems for delivering optical beams onto the fundus, include: (a) laser beam coagulation apparatus in which a laser beam is focused onto tissue in the posterior chamber of an eye to raise the temperature of the tissue to a high enough temperature to cause thermocoagulation and (b) Optical Coherence Tomography ("OCT") apparatus in which a low coherence optical beam obtained, for example, from a superluminescent diode CSLD) is focused onto the fundus and a cross-sectional image of the fundus is obtained using short-coherence interferometry. U.S. Pat. No. 5,067,951 discloses an example of a laser beam coagulation apparatus and an article entitled "Optical Coherence Tomography" by D. Huang et al., *Science*, 254, Nov. 22, 1991, pp. 1178–1181 discloses an example of an OCT apparatus.

The above-identified apparatus typically utilize an optical set-up which is comprised of a slit lamp and an ocular lens. In operation, illumination is provided when the ocular lens, in conjunction with the lens of an eye, forms an aerial fundus image onto the focal plane of the slit lamp. The aerial fundus image is observed through an observation path of the slit lamp optics. In addition, an optical beam is coupled into the slit lamp observation path by a beamsplitter. In these apparatus, the ocular lens is normally held by hand close to a patient's eye or in direct contact with the cornea.

In the slit lamp and ocular lens optical set-up which is typically used in the above-described apparatus, reflection of an illumination beam and an optical beam from the cornea and from the ocular lens is much more intense than reflection from the fundus. For example, reflectivity of the fundus is approximately $10^{-4}$ whereas reflectivity of the cornea and reflectivity of a typical ocular lens (for example, a Volk double aspheric bio lens manufactured by Volk of 7893 Enterprise Drive, Mentor, Ohio 44060) are both on the order of 4%, which value of reflectivity is much greater than the reflectivity of the fundus. Consequently, the quality of a fundus image is degraded by artifacts which result from reflections from the ocular lens and the cornea. In order to remove such artifacts, it is necessary to prevent reflections from the cornea and from the ocular lens from entering the observation path. Present attempts to prevent reflection from the ocular lens from entering the observation path entail tilting the ocular lens with respect to the illumination beam and the optical beam. However, tilting the ocular lens is not satisfactory because it introduces astigmatism and vignetting. In addition, attempts to prevent reflections from the cornea from entering the observation path entail using a contact ocular lens. However, using a contact ocular lens is not satisfactory because it is difficult to eliminate reflection from both the cornea and the ocular lens when a hand-held ocular lens is used. As a result, it is difficult to obtain a good fundus image in apparatus using this type of optical set-up.

Attempts have been made to solve the above-described problem by geometrically separating reflections from the ocular lens and the cornea by using: (a) ring illumination (ring illumination is obtained, for example, by placing a stop in the illumination path to remove the center of the illumination beam) and (b) a small, centered aperture for observing the fundus to geometrically separate reflections from the cornea and the ocular lens. However, using ring illumination is not satisfactory because reflection of the optical beam from the cornea and from the ocular lens cannot be avoided, except if the optical beam diameter is small enough so that it can be coupled into the eye, off-center. However, this is disadvantageous because it requires a large pupil diameter to avoid optical beam vignetting.

In light of the above, there is a need in the art for an ophthalmologic apparatus which: (a) has a simple structure; (b) delivers an optical beam onto the fundus without vignetting; and (c) provides a high quality fundus image.

SUMMARY OF THE INVENTION

Advantageously, embodiments of the present invention overcome the above-described problems in the art and provide an ophthalmologic apparatus which: (a) has a simple structure; (b) delivers an optical beam onto the fundus without vignetting; and (c) provides a high quality fundus image. In particular, an embodiment of the present invention is an optical system which includes three, separated radiation path systems—a tilted illumination path system, a decentered observation path system, and an optical path system—which are combined by a beamsplitter into an ocular lens. In accordance with the present invention, an illumination path provided by the illumination path system and an optical beam path provided by the optical beam path system are obliquely oriented with respect to the optical axis of the ocular lens. As a result: (a) reflections from the ocular lens do not enter the observation path system; (b) specular reflection of illumination from the cornea does not enter the observation path system; and (c) scattering of illumination from corneal stroma does not enter the observation path system.

Advantageously, in accordance with the present invention, the illumination aperture and the observation aperture at the cornea are separated and are located side by side. As a result, a pupil as small as 4 mm in diameter is sufficient to incorporate both the observation aperture and the illumination aperture without vignetting. This is to be compared to a fundus camera where normally a 6 mm diameter pupil is required to accomplish the same effect. As a result, fundus imaging can be performed without having to dilate the eye pupil.

In accordance with the present invention, a stop aperture in the observation path system is decentered with respect to an optical axis of the observation path system and, in the preferred embodiment, the image in the observation path system is relayed by a simple, two-lens system which is almost symmetrically decentered about the stop aperture. This advantageously provides a good fundus image since certain optical aberrations such as, for example, distortion and lateral color are canceled out and coma is minimized.

In accordance with the present invention, for a patient's comfort and for non-dilated eye examination, a near-infrared transmitting filter (720 nm to 1100 nm) can be utilized in conjunction with a tungsten lamp for illumination and a CCD camera for observation. As a result, a fundus image can be seen on a video monitor and the patient can go through a lengthy examination period without suffering the bright illumination which is often utilized with prior art apparatus.

BRIEF DESCRIPTION OF THE FIGURE

FIG. 1 shows, in pictorial form, a top view of an ophthalmologic apparatus for fundus imaging which is fabricated in accordance with the present invention wherein only an illumination path system and an observation path system are shown;

FIG. 2 shows, in pictorial form, a side view of the ophthalmologic apparatus shown in FIG. 1 wherein only the observation path system and the optical beam path are shown;

Components which are the same in the various figures have been designated by the same numerals for ease of understanding.

DETAILED DESCRIPTION

Figure 3:
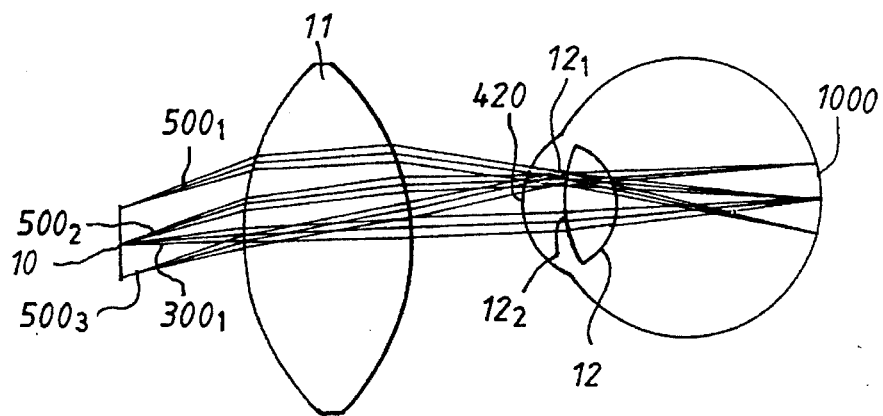
FIG. 3 shows, in pictorial form the direction that radiation from the illumination path system travels from an intermediate image plane to the fundus and the direction that radiation reflected from the fundus travels to the observation path system by way of the intermediate image plane.

FIG. 1 shows, in pictorial form, a top view of ophthalmologic apparatus 600 for fundus imaging which is fabricated in accordance with the present invention wherein only illumination path system 500 and observation path system 300 are shown. As shown in FIG. 1, illumination path system 500 includes light source 1, for example, an incandescent light source, lens 2, for example, a large numerical aperture condenser lens, for collecting radiation output from source 1, and stop aperture 3, for example, a movable slot, which is located at the back focal plane of lens 5. Lens 5 and lens 6 image stop aperture 3 at intermediate image plane 10. Intermediate image plane 10 is located at the back focal plane of lens 6 and radiation between lenses 5 and 6 is in the form of a collimated beam.

In accordance with a preferred embodiment of the present invention, light source 1 is an incandescent light source and illumination path system 500 further includes: (a) near-infrared, transmitting filter 7 and (b) glass prisms 4 and 8. Near-infrared, transmitting filter 7 is, for example, a Schott RG9, 720 nm to 1100 nm, transmitting filter which blocks visible and far infrared light emitted by incandescent source 1 for the patient's safety and comfort. Glass prisms 4 and 8 are placed in illumination path system 500 to fold it into a compact optical package. Further, in the preferred embodiment, beamsplitter 9 has a minus filter coating (to be described in detail below) which transmits near-infrared light and reflects wavelengths used for diagnosis or surgery.

As shown in FIG. 1, ocular lens 11 is movably mounted and, in conjunction with eye lens 12, focuses intermediate image plane 10 onto fundus 1000. The refractive error of a human eye varies within a range of up to ±20 diopters. As is indicated in FIG. 1, ocular lens 11 is movably mounted by means which are well known in the art for axial motion along its optical axis to compensate the refractive power of a patient's eye so that the fundus image is always located at intermediate image plane 10. In accordance with the present invention, stop aperture 3 and intermediate image plane 10 are conjugate and intermediate image plane 10 and fundus 1000 are conjugate. As a result, stop aperture 3 is conjugate to fundus 1000. Thus, the illumination location and illumination field on fundus 1000 can be varied by adjusting the location and size of stop aperture 3. Further, in accordance with the present invention, radiation from illumination path system 500 is incident upon ocular lens 11 at a large angle (tilt) and, as a result, reflections therefrom are efficiently rejected from observation path system 300. However, as shown in FIG. 1, because of the tilt of illumination path system 500 with respect to the optic axis of ocular lens 11, the patient's eye is decentered with respect to ocular lens 11 to ensure that the radiation from an illumination path provided by illumination path system 500 impinges upon the cornea.

As shown in FIG. 1, observation path system 300 is an optical image relay system comprised of lenses 13 and 15. Eye lens 12 and ocular lens 11 form an aerial image of fundus 1000 at intermediate image plane 10. The fundus aerial image at intermediate image plane 10 is then relayed to plane 160 by lenses 13 and 15. Finally, the image formed at plane 160 can be observed by placing CCD camera 470 at plane 160.

As shown in FIG. 1, observation path stop aperture 14 is located between lenses 13 and 15 and lenses 13 and 15 are symmetrically decentered about stop aperture 14. Advantageously, this arrangement cancels distortion and lateral color and minimizes coma. In accordance with a preferred embodiment of the present invention, to achieve substantially perfect optical symmetry so that distortion and lateral color are canceled and coma is minimized, the focal length of lenses 13 and 15 are substantially equal so that they form a one-to-one relay system.

FIG. 2 shows, in pictorial form, a side view of ophthalmologic apparatus 600 wherein only observation path system 300 and optical beam path system 400 are shown. As shown in FIG. 2, optical beam path system 400 is comprised of optical beam source 18, collimating lens 17, orthogonally mounted, galvanometer driven scanning mirrors 16 and 17 which are mounted on a pair of motors (not shown) and scanner lens 14. Scanner lens 14 images optical beam source 18 onto intermediate image plane 10 which, as was explained above, is conjugate to fundus 1000. Scanning mirrors 16 and 17 are used to locate the output from optical beam path system 400 anywhere on fundus 1000.

Figure 8:
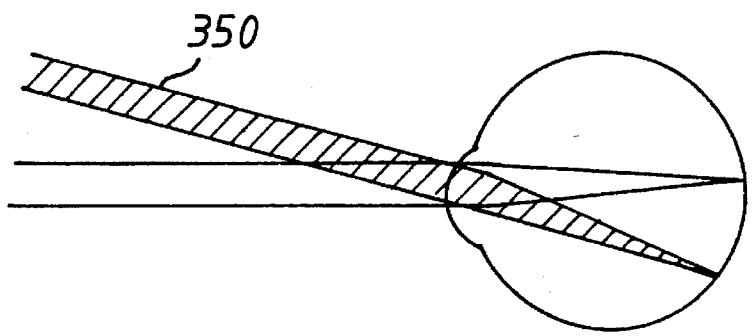
FIG. 8 shows, in pictorial form, non-vignetting during a scan of the optical beam when the optical beam path stop aperture is conjugate to the eye pupil.
Figure 9:
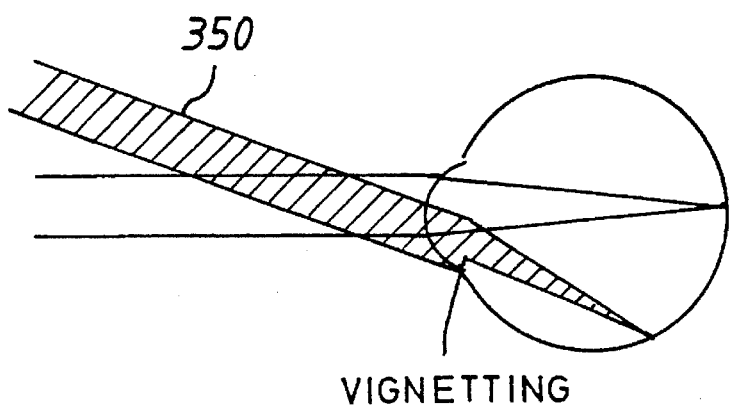
FIG. 9 shows, in pictorial form, vignetting during a scan of the optical beam when the optical beam path stop aperture is not conjugate to the eye pupil.

Optical beam path stop aperture 19 is located on the back focal plane of scanner lens 14 and is imaged to the pupil of eye lens 12. In order to prevent vignetting when the optical beam is scanned, stop aperture 19 should be conjugate with the eye pupil to ensure that the optical beam does not move out of the pupil when it is scanned. For example, see FIG. 8 which shows non-vignetting during a scan of optical beam 350 when stop aperture 19 is conjugate to the eye pupil and FIG. 9 which shows vignetting during a scan of optical beam 350 when aperture 19 is not conjugate to the eye pupil. Since optical beam path stop aperture 19 is located between scanning mirrors 16 and 17, a problem arises because one cannot image both mirrors to the same location. However, one can determine the maximum distance that scanning mirrors 16 and 17 can be separated without causing vignetting for a given ratio of focal length between scanner lens 14 and ocular lens 11. For example, assume that the eye pupil is 4 mm, the scan angle is 30°, i.e., ±15°, and the beam size is 2 mm. For this case, without lenses, the condition for non-vignetting is that the scanning point of the beam be less than 3.7 mm from the pupil. However, using scanner lens 14 having, for example, a focal length of 60 and ocular lens 11 having, for example, a focal length of 12.82, provides a magnification given by the ratio of the focal lengths which enable scanning mirrors 16 and 17 to be separated by as much as 81 mm without causing vignetting. Thus, in accordance with the present invention, the optical path beam will remain non-vignetted during a scan of the fundus if the ratio of the focal length of scanner lens 14 and ocular lens 11 provides sufficient magnification. Since the optical beam is always imaged onto aerial intermediate image plane 10, optical beam system 400, observation path system 300 and illumination path system 500 are said to be parfocal. This means that these three optical beam path systems are always in focus together.

FIG. 3 shows, in pictorial form, the direction that radiation from illumination path system 500 travels from intermediate image plane 10 to fundus 1000 and the direction that radiation reflected from fundus 1000 travels to observation path system 300 by way of intermediate image plane 10. As shown in FIG. 3, ray bundles $500_1$, $500_2$, and $500_3$ represent radiation from illumination path system 500 and aperture $12_1$ represents the aperture of illumination path system 500 on cornea 420 of eye lens 12. Further, ray bundle $300_1$ represents radiation transmitted to observation path system 300 and aperture $12_2$ represents the aperture of observation path system 300 on cornea 420 of eye lens 12. It is important to note, as shown in FIG. 3, that ray bundles $500_1$, $500_2$, and $500_3$ from illumination path system 500 are focused by ocular lens 11 onto eye lens 12 in an off-center configuration. Hence, the illumination path provided by illumination path system 500 and the observation path provided by observation path system 300 are separated in the anterior chamber of the eye and almost no light from illumination path system 500 is scattered back into observation path system 300.

In accordance with the present invention, embodiments are fabricated wherein: (a) illumination aperture $12_1$ and observation aperture $12_2$ are geometrically separated in the pupil of the eye (as a result, scattering of radiation from illumination path system 500 by cornea stroma will not be observed in observation path system 300) and (b) illumination aperture $12_1$ and observation aperture $12_2$ are separated and are located side by side in such a manner that a pupil as small as 4 mm in diameter is sufficient to incorporate both apertures without vignetting. These advantageous effects are achieved by balancing the following two considerations. The first consideration used in fabricating embodiments of the present invention is to obliquely orient, i.e., tilt the illumination path provided by, illumination path system 500 relative to ocular lens 11 so that specular reflection will not enter observation path system 300. As discussed above, this requires that the patient's eye be decentered with respect to ocular lens 11. The second consideration used in fabricating embodiments of the present invention is to locate observation aperture $12_2$ as close as possible to illumination aperture $12_1$ so that a minimum pupil diameter will be needed to accommodate both apertures. This second consideration produces a design which requires decentering observation stop aperture $12_2$ with respect to the optic axis of ocular lens 11 and lens 13. Since stop aperture 14 is conjugate to observation aperture $12_2$, the decentering of observation aperture $12_2$ is accomplished by decentering stop aperture 14 with respect to the optic axis of lens 11. As a result, there is a design tradeoff in that, by achieving better reflection rejection by tilting the illumination path provided by illumination path sustem 500, the minimum pupil diameter needed to accommodate both illumination aperture $12_1$ and observation aperture $12_2$ increases if we want to limit the amount of decentering of stop aperture 14. One must also keep in mind that it is desired to limit decentering of stop aperture 14 because larger decentering requires a larger diameter for lenses 13 and 14 and, hence, larger cost. If one were to center stop aperture 14 with respect to the optic axis, there would be incomplete overlap of the illumination and observation fields of view on fundus 1000. This would result in a diminished image intensity. The incomplete overlap results from the fact that the eye is decentered with respect to ocular lens 11 for the reasons discussed above. In addition, such a centering of stop aperture 14 would increase the size of the pupil diameter needed to accommodate both illumination aperture $12_1$ and observation aperture $12_2$.

Figure 4:
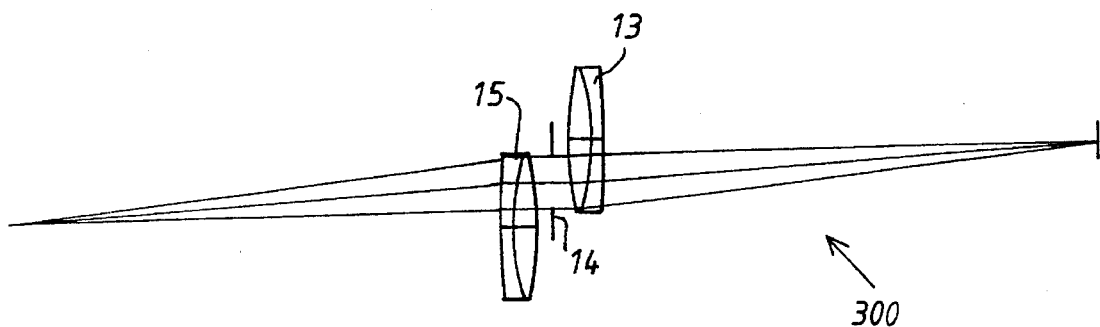
FIG. 4 shows, in pictorial form, relay optics utilized in the observation path system of the inventive ophthalmologic apparatus.

FIG. 4 shows, in pictorial form, relay optics utilized in observation path system 300, which relay optics is comprised of lenses 13 and 15. As shown in FIG. 4, lenses 13 and 15 are symmetrically decentered about decentered stop aperture 14 so that distortion and lateral color are completely eliminated and coma has been significantly reduced. In accordance with the present invention, stop aperture 14 is conjugate to observation aperture $12_2$ shown in FIG. 3. As was discussed above, observation aperture $12_2$ is decentered so that illumination aperture $12_1$ and observation aperture $12_2$ can be placed close to each other. As stop aperture 14 is moved up, as seen in FIG. 3, observation aperture $12_2$ moves down, and vice versa. Thus, stop aperture 14 is decentered with respect to the optical axis of observation path 300 in order to decenter observation aperture $12_2$ with respect to the optical axis of ocular lens 11. This configuration can be very useful for a binocular observation system since both apertures have to be decentered in such an observation system.

Figure 5:
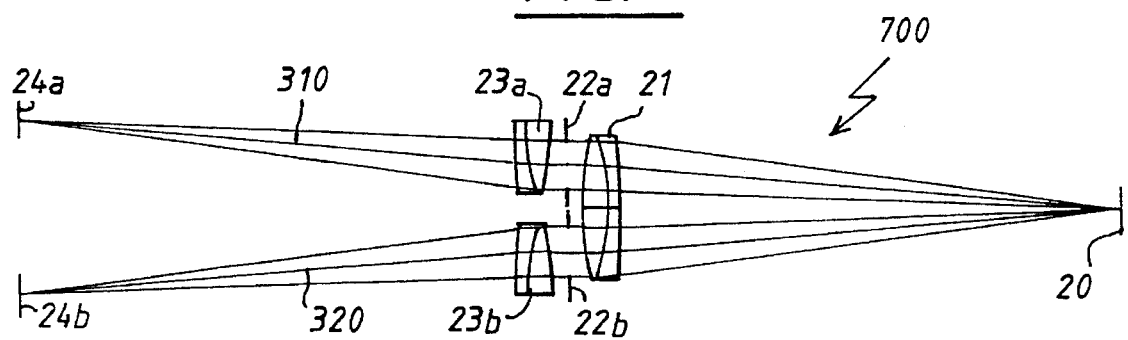
FIG. 5 shows an embodiment of a binocular observation path system for use in fabricating embodiments of the present invention.

FIG. 5 shows, in pictorial form, an embodiment of binocular observation path system 700 for use in fabricating embodiments of the present invention. As shown in FIG. 5, object 20 is located at the focal plane of objective lens 21 and stop apertures 22.a and 22.b for observation path systems 310 and 320, respectively, are symmetrically located between objective lens 21 and lenses 23.a and 23.b, respectively. In a preferred embodiment of the present invention, lenses 23.a and 23.b are identical to the halves of lens 21 and are formed by cutting a lens which is identical to lens 21 in half; lens 23.a corresponds to the lower half of lens 21 and lens 23.b corresponds to the upper half of lens 21. Then, as shown in FIG. 5, object 20 is relayed into image planes 24.a and 24.b. Stereoscopic observation can be achieved by slightly tilting lens 23.a and 23.b relative to objective lens 21 symmetrically. Then, image planes 24.a and 24.b can be observed through a binocular eye piece (not shown) or CCD cameras.

Figure 6:
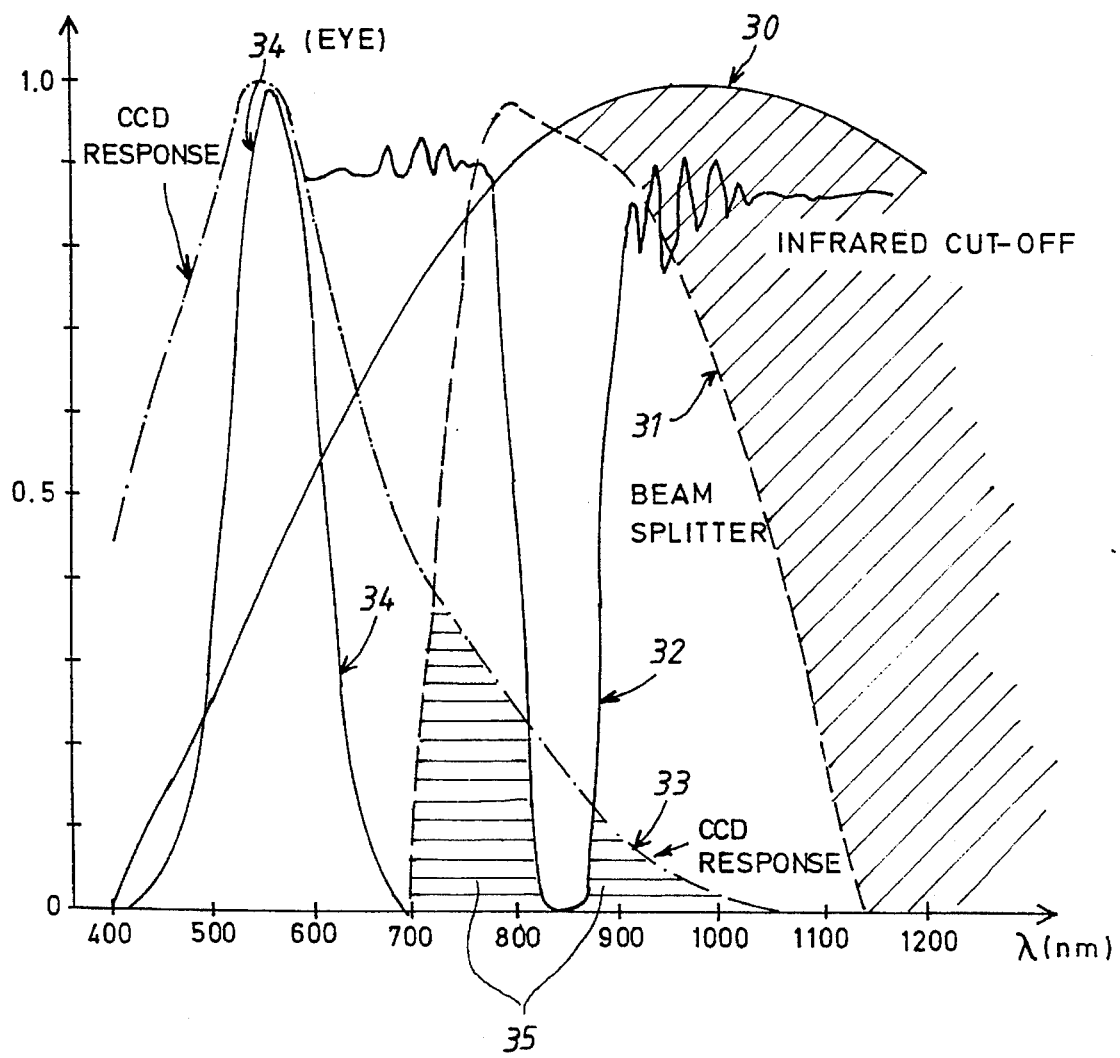
FIG. 6 shows an embodiment of a coating for a beamsplitter for use in fabricating embodiments of the present invention with an optical beam having a center wavelength at about 850 nm and a spectral width of less than about 40 nm.

FIG. 6 shows an embodiment of a coating for beamsplitter 9 for use in fabricating embodiments of the present invention with an optical beam having a center wavelength at about 850 nm and a spectral width of less than about 40 nm. Curve 30 represents the output from a tungsten light bulb at 3000° K. RG9 filter curve 31 transmits from about 720 nm to about 1100 nm. Curve 34, showing the response of an eye, shows that radiation transmitted by the RG9 filter is barely visible to the eye and any such light which is visible has a deep reddish color to the eye. Since coating 32 is designed for an optical beam having a wavelength centered at 850 nm, beamsplitter 9 will not transmit illumination from 820 to 870 nm. The observation is obtained by using a CCD camera having a response given by curve 33. The resulting response curve is shown as grid area 35.

Figure 7:
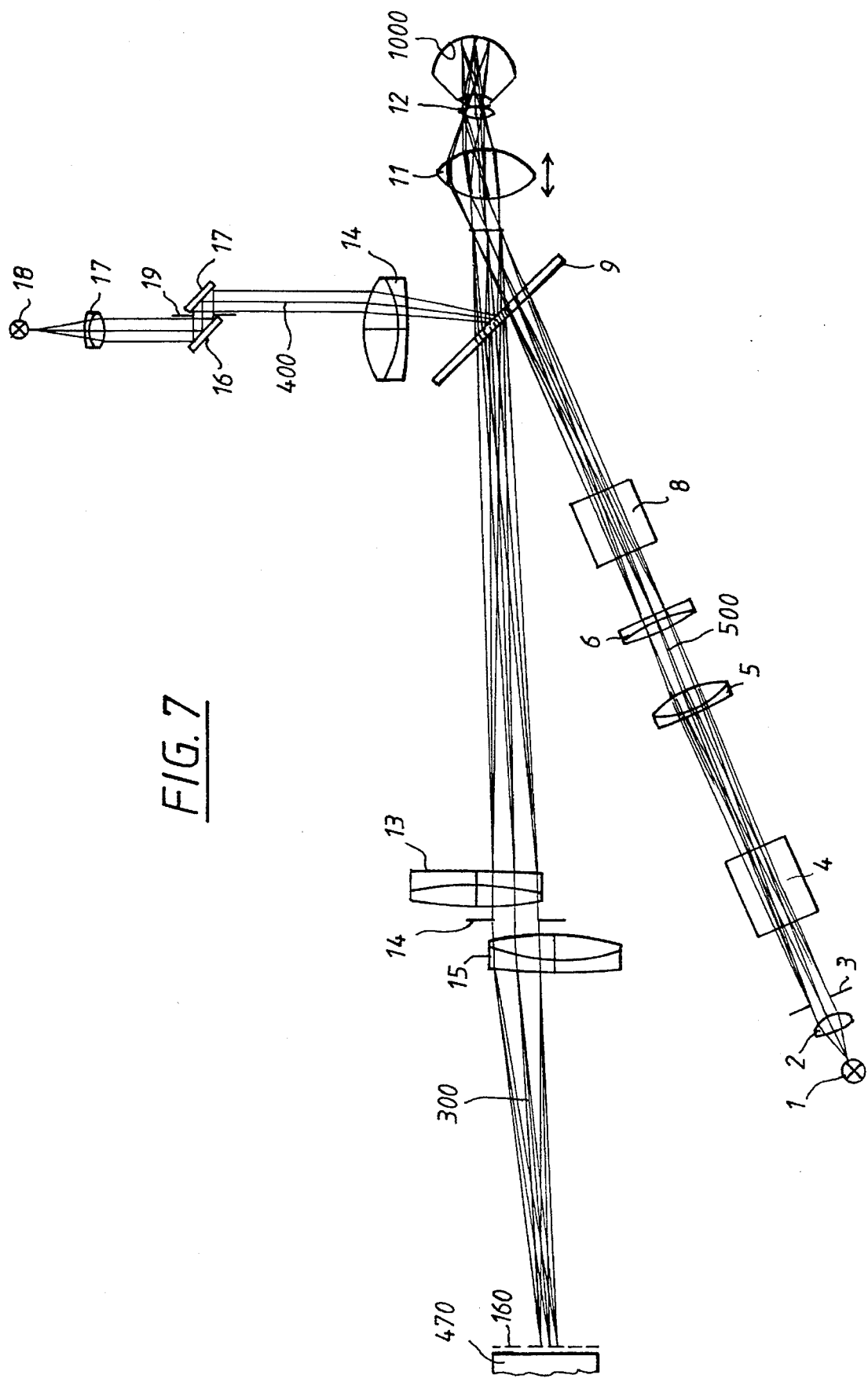
FIG. 7 shows, in pictorial form, a side view of an alternative embodiment of the inventive ophthalmologic apparatus.

FIG. 7 shows, in pictorial form, a side view of an alternative embodiment of the inventive ophthalmologic apparatus. In the optical set-up shown in FIG. 7, the tilt and decenter are arranged in the vertical plane (and the field of view and illumination are limited in the tilt and decenter plane) instead of being arranged in the horizontal plane as was the case for the embodiment shown in FIG. 1. Since a CCD chip typically has a format which is larger in the horizontal than in the vertical direction, normally a 4:3 ratio, it is advantageous to arrange the optical set-up to have a limited field of view in the vertical direction and to use the full CCD pixels in the horizontal direction.

Those skilled in the art will recognize that the foregoing description has been presented for the sake of illustration and description only. As such, it is not intended to be exhaustive or to limit the invention to the precise form disclosed. For example, modifications and variations are possible in light of the above teaching which are considered to be within the spirit of the present invention. Thus, it is to be understood that the claims appended hereto are intended to cover all such modification and variations which fall within the true scope and spirit of the invention.

What is claimed is:

1. Apparatus for illuminating and examining a fundus of an eye which comprises:

three, separated radiation path systems; an illumination path system for providing an illumination path, an observation path system for providing an observation path, and an optical beam path system for providing an optical beam path, wherein the radiation paths provided by the radiation path systems are coupled by combining means and an ocular lens means to the eye; wherein the illumination path system and the optical beam path system are disposed so that the illuminating path and the optical beam path are obliquely oriented with respect to an optical axis of the ocular lens means.

2. The apparatus of claim 1 wherein the illumination path is obliquely oriented with respect to the optical axis of the ocular lens to cause an aperture of the illumination path system to be formed on a cornea of the eye so that reflection from the eye and the ocular lens means is substantially prevented from entering the observation path system.

3. The apparatus of claim 2 wherein a stop aperture of the observation path system is disposed to cause an aperture of the observation path system to be formed on the cornea.

4. The apparatus of claim 3 wherein the stop aperture of the obligation path system is decentered with respect to the optic axis of the ocular lens means so that the aperture of the observation path system on the cornea and the aperture of the illumination path system on the cornea are geometrically separated in a pupil of the eye.

5. The apparatus of claim 4 wherein the observation path system further comprises an observation relay optic system for relaying an image of the fundus formed at an intermediate image plane which is conjugate to the fundus, which relay optic system is comprised of a pair of lens means which are substantially symmetrically decentered with respect to the stop aperture of the observation path system.

6. The apparatus of claim 5 wherein the illumination path system comprises an illumination relay optic system for forming an image of an illumination path stop aperture at the intermediate image plane.

7. The apparatus of claim 6 wherein the illumination path stop aperture is movable and the size is variable for varying the size and field of illumination radiation transmitted to the fundus from the illumination path system.

8. The apparatus of claim 7 wherein the illumination path system further comprises a light source and filter means for transmitting a predetermined portion of a spectrum of radiation generated by the light source.

9. The apparatus of claim 8 wherein the light source is an incandescent source and the filter means is a filter for transmitting radiation in the near-infrared.

10. The apparatus of claim 6 wherein tile optical beam path system comprises an optical beam source, means for scanning radiation from the optical beam source, scanner lens means for transferring radiation from the scanned beam to impinge upon the combining means to form an image of the optical beam source image on the intermediate image plane.

11. The apparatus of claim 10 wherein an optical beam path stop aperture lies on a back focal plane of the scanner lens means.

12. The apparatus of claim 11 wherein the scanning means comprises a pair of orthogonally mounted scanning mirrors and the optical beam path stop aperture is located between the scanning mirrors.

13. The apparatus of claim 12 wherein the ratio of the focal lengths of the scanner lens means and the ocular lens means is larger than 4.

14. The apparatus of claim 12 wherein a ratio of a focal length of the scanner lens means and a focal length of the ocular lens means and a separation between the scanning mirrors provide that the stop aperture of the optical beam path system is substantially conjugate to the pupil.

15. The apparatus of claim 6 which further comprises a CCD camera disposed in the observation path.

16. The apparatus of claim 15 wherein the CCD camera is comprised of a CCD chip having a vertical direction and a horizontal direction and wherein the oblique orientation of the illumination path with respect to the optical axis of the ocular lens means and the decentering of the stop aperture of the observation path system with respect to the optic axis of the ocular lens means occur in a vertical direction which corresponds to the vertical direction of the CCD chip.

17. The apparatus of claim 3 wherein the stop aperture of the observation path system is decentered with respect to the optic axis of the ocular lens means so that the aperture of the observation path system on the cornea and the aperture of the illumination system on the cornea are geometrically separated and are located side by side so that a pupil of the eye having a predetermined diameter incorporates both apertures without vignetting.

18. The apparatus of claim 2 wherein the observation path system provides a binocular radiation path and comprises a first and a second stop aperture, each of which is decentered with respect to the optic axis of the ocular lens means.

19. The apparatus of claim 1 wherein the combining means comprises a beamsplitter.

\* \* \* \* \*